(12) United States Patent
Aiki et al.

(10) Patent No.: US 6,771,075 B2
(45) Date of Patent: Aug. 3, 2004

(54) AIR ION MEASURING DEVICE

(75) Inventors: Yoshiaki Aiki, Tokyo (JP); Shunichi Takahashi, Aomori (JP)

(73) Assignee: Andes Electric Co., Ltd., Hachinohe (JP)

( * ) Notice: Subject to any disclaimer, the term of this patent is extended or adjusted under 35 U.S.C. 154(b) by 18 days.

(21) Appl. No.: 10/173,761

(22) Filed: Jun. 19, 2002

(65) Prior Publication Data

US 2003/0001584 A1 Jan. 2, 2003

(30) Foreign Application Priority Data

Jun. 27, 2001 (JP) ........................................ 2001-194418

(51) Int. Cl.[7] .............................................. G01N 27/62
(52) U.S. Cl. ...................................... 324/464; 324/459
(58) Field of Search ................................ 324/464, 459; 250/385.1

(56) References Cited

U.S. PATENT DOCUMENTS 4,853,536 A * 8/1989 Dempsey et al. ........... 250/253
5,728,288 A * 3/1998 Kubo ........................ 205/763
6,331,706 B1 * 12/2001 Orr et al. ................. 250/385.1
6,465,777 B1 * 10/2002 Rache ........................ 250/287

* cited by examiner

*Primary Examiner*—N. Le
*Assistant Examiner*—John Teresinski
(74) *Attorney, Agent, or Firm*—Wenderoth, Lind & Ponack, L.L.P.

(57) ABSTRACT

An air ion measuring device is provided which holds the air passage rate in an ion detector as constant as possible to provide for improved air ion measurement reliability, permits a size and thickness reduction and also a reduction of parts and cost of the ion detector, permits ready cleaning thereof, provides a measure for coping with static electricity, provides good visual recognition property in the air ion data display and displays data other than air ion data and error data. An ion detector structure is formed by disposing a charge collector electrode and repelling electrodes in the vicinity of opposite ends of the charge collector electrode on one side surface of an air passage, through which air is withdrawn from one end portion and exhausted from the other end portion, and disposing a further repelling electrode on the other side surface of the air passage.

12 Claims, 7 Drawing Sheets

AIR ION MEASURING DEVICE

BACKGROUND OF THE INVENTION

1. Field of the Invention

Up to date, the importance of ions is recognized in various fields such as health fields, pollution fields and foodstuff fields as well as medical fields.

Many devices and tools having an ion generator or an ion generating function to generate negative ions are used in homes, offices, plants, etc. The invention relates to air ion measuring devices, which are compact in construction and capable of accurately measuring the quantities of positive and negative ions contained in air in the above circumstances readily permitting the recognition of the results of measurements.

2. Prior Art

Figure 12:
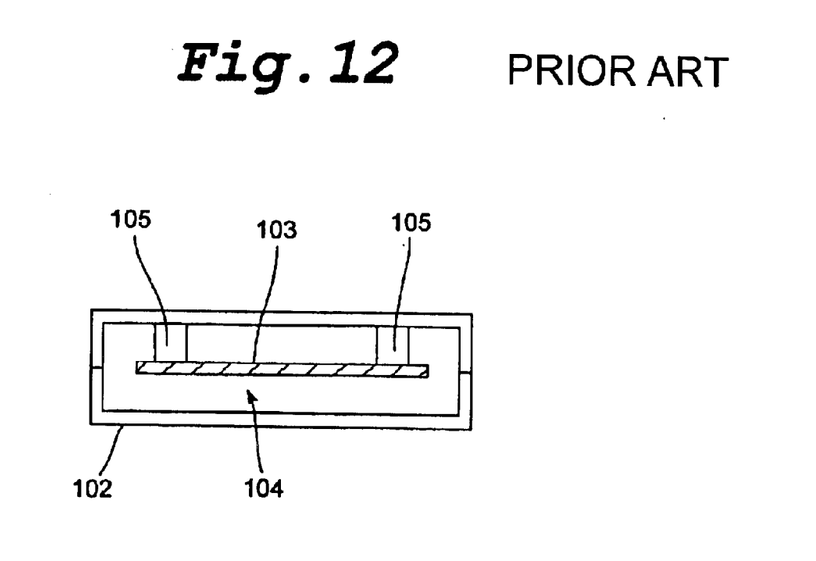
FIG. 12 is a schematic sectional view showing a state of disposition of various electrodes in a prior art air ion measuring device.
Figure 13:
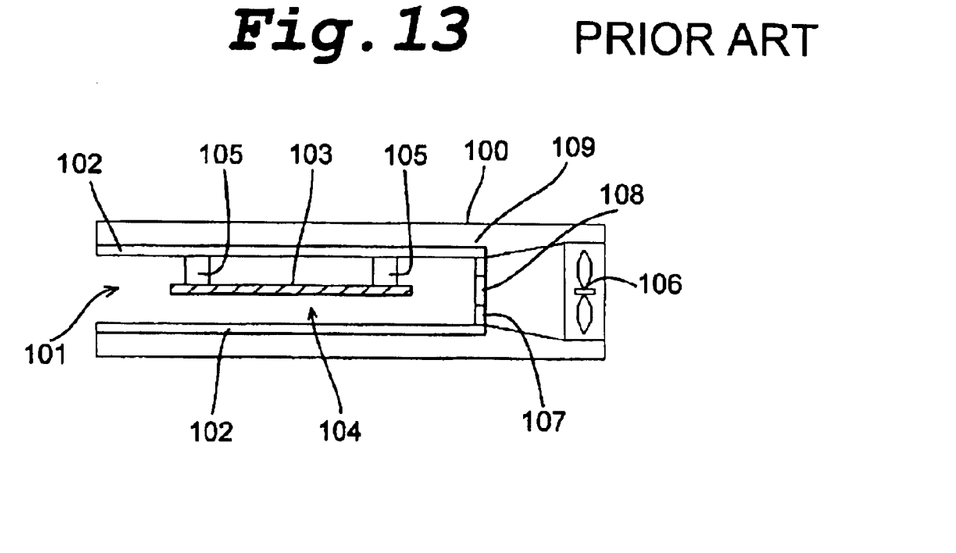
FIG. 13 is a schematic sectional view showing the internal construction of a prior art air ion measuring device.
Figure 14:
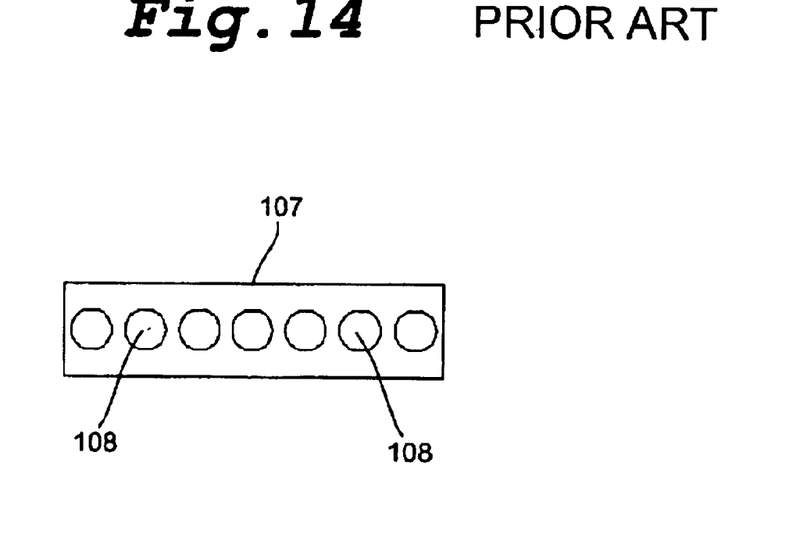
FIG. 14 is a schematic plan view showing a partitioning member structure of a prior art air ion measuring device.

FIGS. 12 to 14 shows a prior art ion measuring device. The device comprises an ion detector 104, which has such a construction that it includes a cylindrical repelling electrode 102 provided on the inner surface of an air passage 101 formed in a cylindrical case 100 for withdrawing air formed in one end portion and exhausting the withdrawn air from the other end portion and a charge collector electrode 103 disposed at the center of the air passage 101. As an alternative construction, the ion detector 104 includes a pair of flat repelling electrodes 102 and a charge collector electrode 103 disposed mid way between the repelling electrodes 102. Reference numeral 105 designates posts for holding the charge collector electrodes 103.

Reference numeral 106 designates an air withdrawal fan, which is disposed in the other end portion of the air passage 101 opposing the air inlet in the afore-mentioned end portion in such orientation as to withdraw air in the same direction as the air passage direction. Reference numeral 107 designates a partitioning member, which is disposed at the outlet of the ion detector 104 and has a plurality of pores 108 for adjusting the air passage rate. Reference numeral 109 designates an air fitting, which constitutes a casing fitted on the repelling electrode or electrodes of the ion detector 104 provided on the surface of the air passage 101 and also on an air passage portion extending from the outlet of the ion detector 104 to the air withdrawal fan 106.

For measuring, for instance, negative ions in air with the above construction, air is passed through the air passage 101 by driving the air withdrawal fan 106 with the repelling electrode or electrodes 102 held negatively charged. In this way, negative ions in air passing by the repelling electrode or electrodes 102 are repelled to be more readily collected on the charge collector electrode 103, while positive ions are attracted to and neutralized by the negatively charged repelling electrode or electrodes 102. The charge collected on the charge collector electrode 103 is converted to voltage and measured. The measurement of positive ions may be made in like principles by positively charging the repelling electrode or electrodes.

In the prior art air ion measuring device having the above construction, however, the charge collector electrode is supported in a hanged state in the air passage at the center of the cylindrical repelling electrode or midway between the flat repelling electrodes. Inevitably, the thickness of the ion detector is correspondingly increased, and this dictates size increase of the measuring device itself. In addition, the number of components is increased by parts for holding the charge collector electrode, thus correspondingly dictating many steps of operation and much labor in manufacture. Furthermore, the structure itself constitutes a cause of cleaning difficulty. Furthermore, since the air withdrawal fan is oriented such as to withdraw air in the same direction as the air passage direction, it also constitutes a cause of thickness increase of the device itself.

Moreover, the disposition of the charge collector electrode as noted above does not only lead to an increase in the number of parts but also provides resistance offered to the air passage and causes disturbance thereof, which is undesired from the standpoint of accurate ion quantity measurement.

Likewise, the partitioning member for air passage rate adjustment, which is provided at the outlet of the ion detector, causes disturbance of air passage and is thus again undesired from the standpoint of accurate ion quantity measurement.

Still further, none of prior art portable air ion measuring devices could provide simultaneous display or graphic display of positive and negative ions. Also, none of prior air ion measuring devices could display relative humidity, temperature and atmospheric air pressure which may serve as important parameters for the quantity of air ions generated or could display date, time, etc.

SUMMARY OF THE INVENTION

The invention has an object of providing an air ion measuring device, which can solve all the above problems inherent in the prior art, can hold the air passage rate in an ion detector as constant as possible to improve the reliability of the air ion measurement while permitting reduction of its size and thickness and reduction of the ion detector parts cost, permits ready cleaning of the ion detector and is excellent in air ion data display, provides satisfactory coping with static electricity and good visual recognition property. According to the invention, this object is attained by an ion detector structure including an air passage, through which air is withdrawn from one end portion and exhausted from the other end portion, a charge collector electrode and repelling electrodes disposed in the neighborhood thereof, these electrodes being disposed on one side surface of the air passage, and a repelling electrode disposed on the other side surface of the air passage.

DETAILED DESCRIPTION OF THE PREFERRED EMBODIMENTS

Preferred embodiments of the invention will now be described with reference to the drawings.

Figure 1:
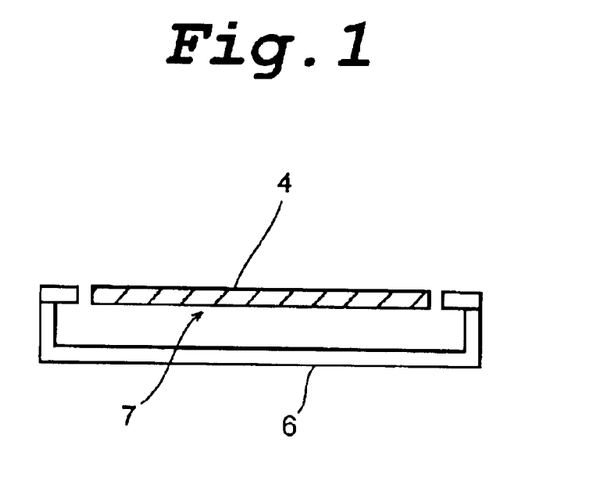
FIG. 1 is a schematic sectional view showing the state of disposition of various electrodes in an air ion measuring device according to the invention.
Figure 2:
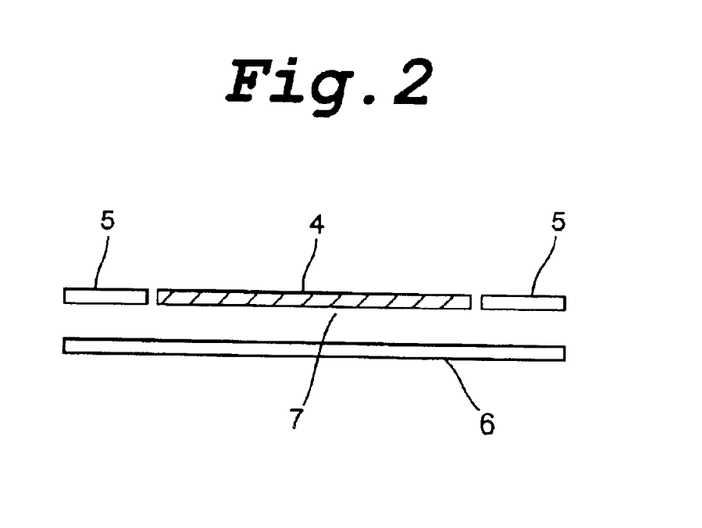
FIG. 2 is a schematic sectional view showing the state of disposition of various electrodes in an air ion measuring device according to the invention.
Figure 3:
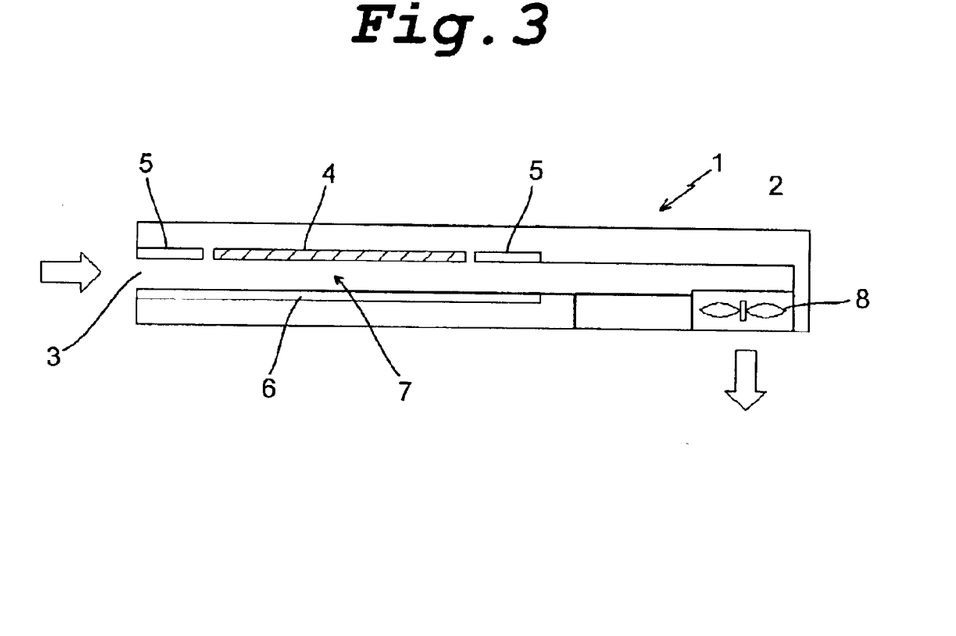
FIG. 3 is a schematic sectional view showing the internal construction of an air ion measuring device according to the invention.

FIGS. 1 to 3 show the internal construction of an air ion measuring device according to the invention.

Referring to the Figures, reference numeral 1 designates the body of the air ion measuring device according to the invention. Reference numeral 2 designates a cylindrical case. In this embodiment, the cylindrical case 2 is an angular cylindrical case, which defines an air passage 3, through which air is withdrawn from an end portion and exhausted from the other end portion. On a portion of the surface of the air passage 3 are disposed a charge collector electrode 4 and repelling electrodes 5 near the opposite ends of the charge collector electrode 4. A further repelling electrode 6 is disposed on a surface portion opposing the charge collector electrode 4 and repelling electrodes 5. The air passage and the electrodes noted above constitute an ion detector 7. Reference numeral 8 designates an air withdrawal fan, which is disposed on the other end portion of the air passage 3 for withdrawing air from one end portion of the air passage and exhausting the withdrawn air from the other end portion. According to the invention, the fan is disposed laterally with respect to the air withdrawal direction, that is, having the same orientation as the air passage direction.

Figure 4:
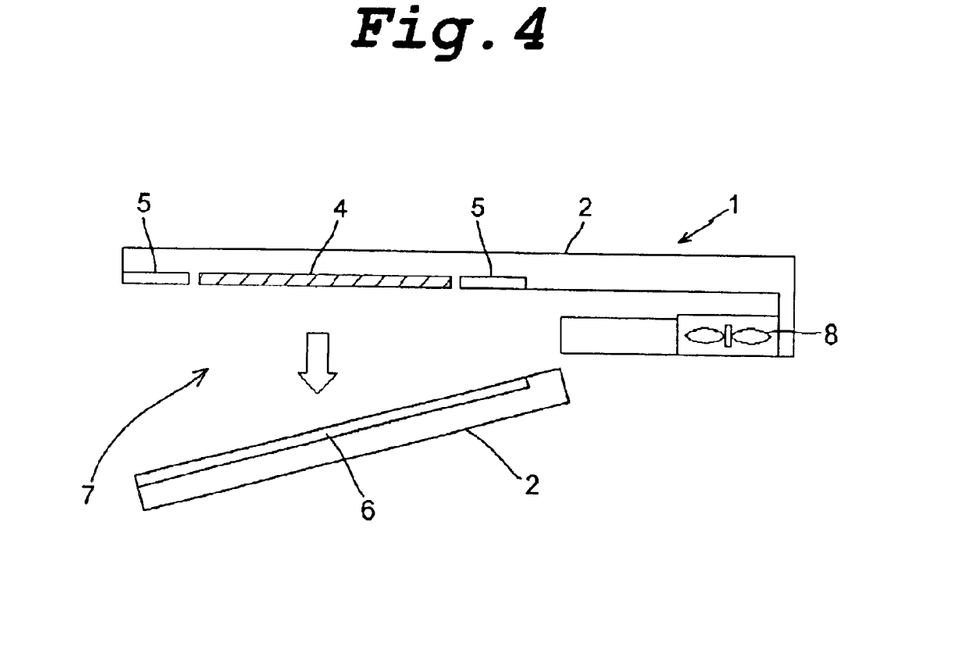
FIG. 4 is a schematic sectional view showing an open/closed state of an ion detector in an air ion measuring device according to the invention.

The outer surface of the ion detector 7 in the cylindrical case 2 is constituted by the resin material constituting the cylindrical case. As shown in FIG. 4, the ion detector 7 having such a construction has a lid portion which can be opened and closed.

As shown in FIGS. 1 to 4, the air passage 3 in the ion detector 7 has a structure having flat side surfaces free from raised and recessed portions for suppressing air passage disturbances and reducing measurement data fluctuations.

Figure 5:
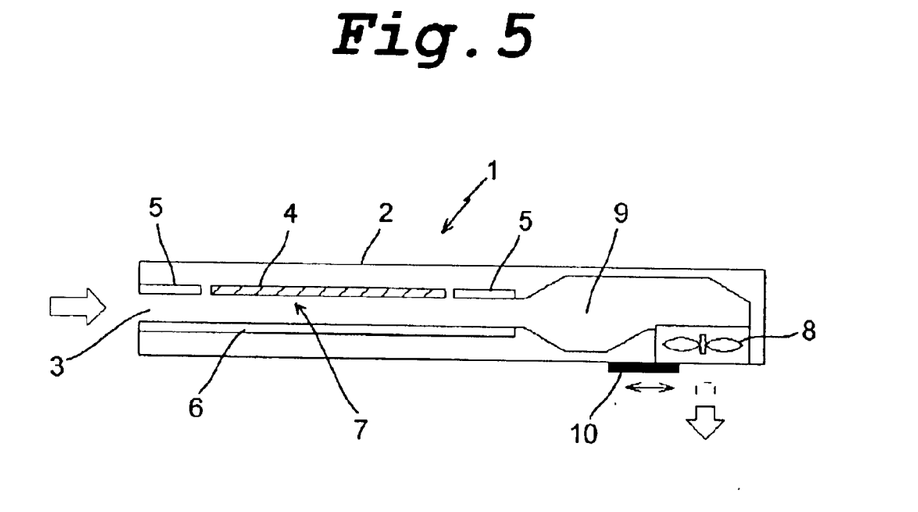
FIG. 5 is a schematic sectional view showing the internal construction of an air ion measuring device according to the invention.

FIG. 5 shows a different embodiment. In the Figure, reference numeral 9 designates an air passage rate adjustment part, which is formed between the trailing end of the ion detector 7 in the air passage 3 and the location of the air withdrawal fan 8. In this part, the air passage 3 is increased in sectional size to reduce the air passage rate and provide rectification so as to reduce measurement data fluctuations.

Reference numeral 10 designates an air quantity adjustment part, which is provided right before or right after the air withdrawal fan and permits air withdrawal adjustment without having any adverse effect on the ion detector.

Figure 6:
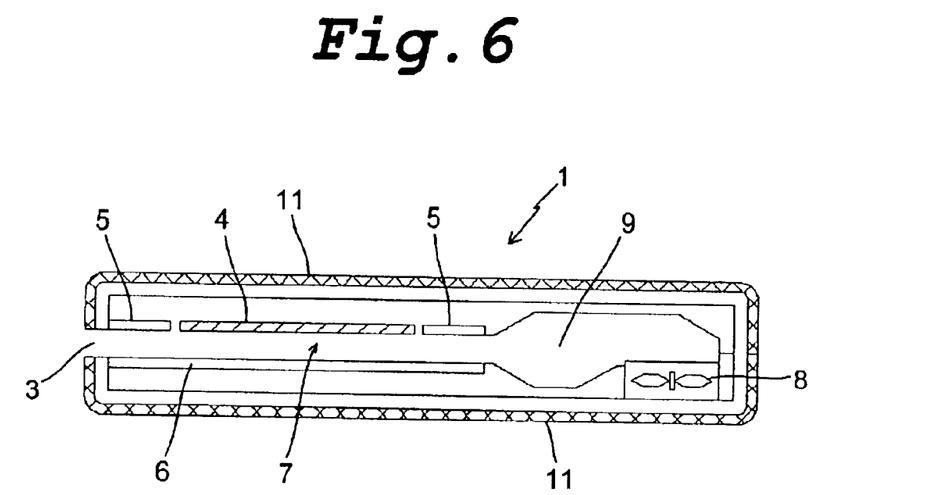
FIG. 6 is a schematic sectional view showing the internal construction of an air ion measuring device according to the invention.

FIG. 6 shows a further embodiment. In this case, the resin material outer surface constituting the cylindrical case 2 on the outer surface of the ion detector 7 is covered by an electrically conductive material 11, thus providing double-wall structure which is free from adverse effects of static electricity.

Figure 7:
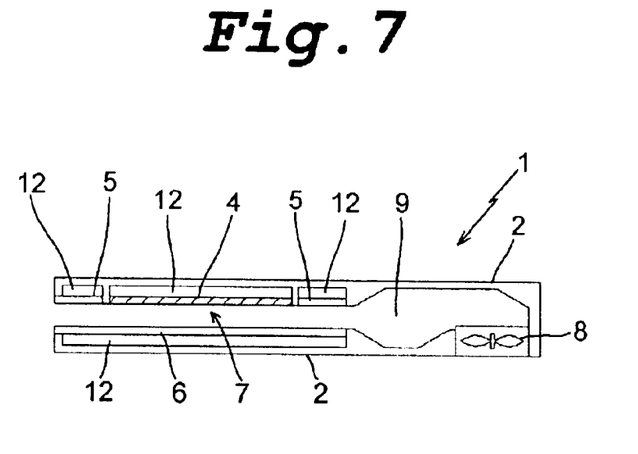
FIG. 7 is a schematic sectional view showing the internal construction of an air ion measuring device according to the invention.

FIG. 7 shows a further embodiment. In this case, a hollow part 12 is formed between the electrodes, i.e., the charge collector electrode 4 and the repelling electrodes 5 and 6, in the ion detector 7, and the resin casing constituting the cylindrical case 2 on the outer side of the electrodes. The hollow part 12 serves to prevent internal charging as much as possible.

Figure 8:
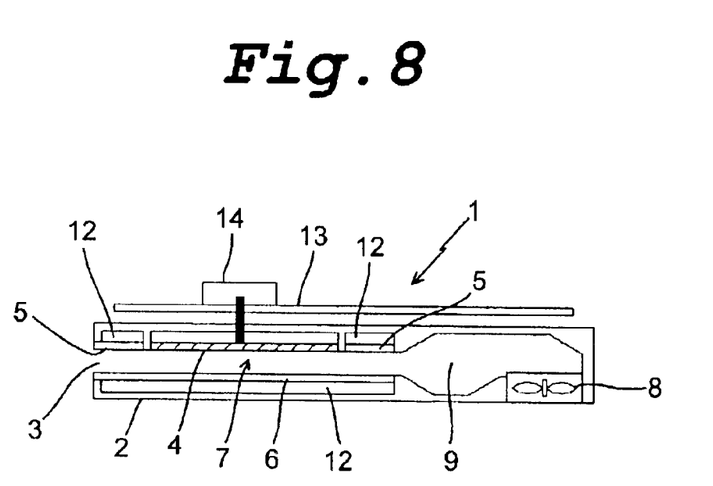
FIG. 8 is a schematic sectional view showing the internal construction of an air ion measuring device according to the invention.

FIG. 8 shows a further embodiment. In this case, a detecting part on an ion detecting circuit 14 mounted on a control board 13 is disposed to be closest to a contact of the charge collector electrode 4, thus preventing as much as possible adverse effects of noise due to the provision of circuit and lead lines therefrom.

Figure 9:
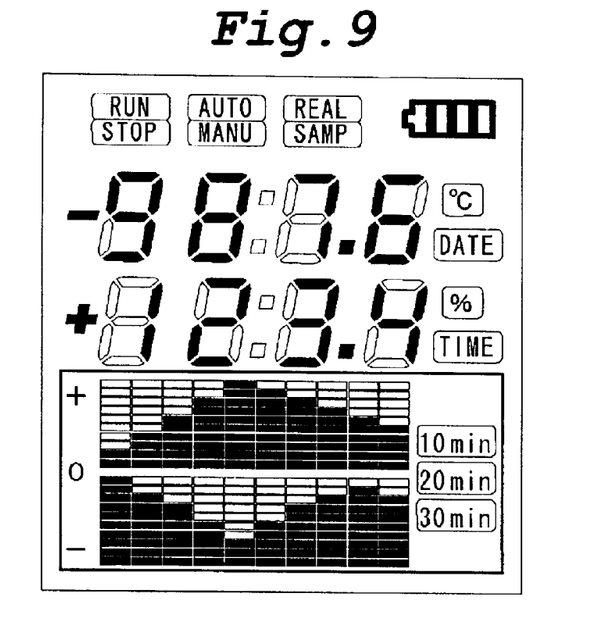
FIG. 9 is a schematic plan view showing a display part in an air ion measuring device according to the invention.

According to the invention, it is possible, as shown in FIG. 9, to provide both a numerical value display and a graphic display of positive and negative air ions, so that the balance between the positive and negative air ions can be recognized at a glance.

Figure 10:
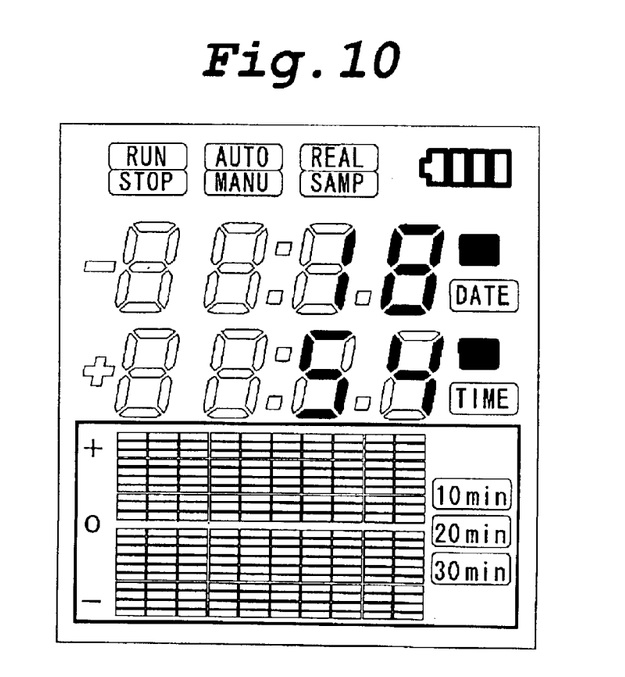
FIG. 10 is a schematic plan view showing the display part of an air ion measuring device according to the invention.

Also, as shown in FIG. 10, it is possible to display temperature, relative humidity, time, atmospheric air pressure, etc. as well as air ion data by providing various sensors and clock IC.

Figure 11:
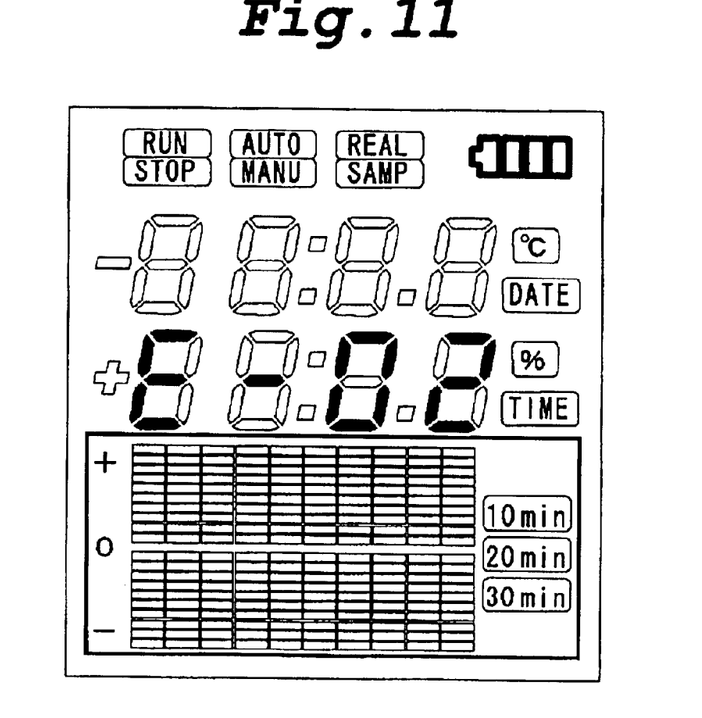
FIG. 11 is a schematic plan view showing the display part of an air ion measuring device according to the invention.

Furthermore, as shown in FIG. 11, it is possible to display, by utilizing a numerical display part, the battery usage, ion detector abnormality (such as short-circuit due to foreign particles), cautions other than working environment and so forth.

For measuring, for instance, negative ions in air with the above construction, air is passed through the air passage 3 by driving the air withdrawal fan 8 with the repelling electrodes 5 and 6 held negatively charged. In this way, negative ions in air are repelled to be more readily collected on the charge collector electrode 4, while positive ions are attracted to and neutralized by the negatively charged repelling electrodes 5 and 6. The charge collected on the charge collector electrode 4 is converted to voltage and measured.

In the prior art ion detector, the charge collector electrode is disposed at the center of the cylindrical repelling electrode or mid way between a pair of flat conversion electrodes. According to the invention, the charge collector and repelling electrodes are disposed on one side of the structure. Thus, it is possible to reduce the thickness of the device and also reduce the number of components to reduce cost.

In addition, the air withdrawal fan is oriented laterally with respect to the air withdrawal direction, thus permitting size and thickness reduction of the air ion measuring device body.

Furthermore, the ion detector has a lid portion capable of being opened and closed, thus permitting ready cleaning of the ion detector and prevention of dust particles from being attached in the inside. It is thus possible to obtain accurate measurement results at all times.

Still further, the ion detector has the structure having flat side surfaces free from recessed or raised portions, and is also provided with the air passage rate adjustment part and the air quantity adjustment part. Thus, it is possible to hold a constant air passage rate, and also the ion mobility is constant. It is thus possible to increase the reliability of measurement and improve the accuracy of the measurement results.

Yet further, such measures as the double-wall structure for coping with static electricity, the hollow part as a charging prevention measure and the disposition of the detecting part of the ion detection circuit in the vicinity of the contact of the charge collector electrode as a measure for preventing noise due to the presence of circuit and lead lines therefrom, are provided. It is thus possible to obtain air ion measurement having improved accuracy.

Moreover, according to the invention the positive and negative ion data are displayed by graphic display as well as numerical value display, thus permitting recognition of the balance between the positive and negative ions at a glance. It is thus possible to provide the user with a good visual recognition property to instantly recognize and grasp the air ion state. Also, it is made possible to display other parameters than the air ion state, such as temperature, relative humidity, date, time and atmospheric air pressure by the provision of various sensors and clock IC. It is further made possible to display such items as battery usage, detecting part abnormality (such as short-circuit due to foreign particles) and cautions other than working environments by making use of a numerical display art. Thus, for the user of the air ion measuring device according to the invention, not only air ion measurement is obtainable, but also many other useful data are made available at hand.

What is claimed is:

1. An air ion measuring device comprising: an ion detector including
    an air passage having a first end portion and a second end portion, wherein air is withdrawn from the first end portion and exhausted from the second end portion,
    a charge collector electrode having a first end and a second end,
    a first repelling electrode disposed in the vicinity of the first end of the charge collector electrode, and a second repelling electrode disposed in the vicinity of the second end of the charge collector electrode, wherein the charge collector electrode and the first and second repelling electrodes are disposed on a first side surface of the air passage, and
    a third repelling electrode disposed on a second side surface of the air passage.

2. The air ion measuring device according to claim 1, wherein the air passage has a fan disposed in the second end portion and oriented laterally with respect to an air withdrawal direction.

3. The air ion measuring device according to claim 1, wherein the ion detector has a lid portion capable of being opened and closed.

4. The air ion measuring device according to claim 1, wherein the air passage in the ion detector has a structure of flat side surfaces free from recessed or raised portions to suppress air passage disturbance and reduce measurement data fluctuations.

5. The air ion measuring device according to claim 1, wherein the air passage comprises:
    a first portion having a first sectional area, and
    a second portion having a second sectional area, wherein the first sectional area differs from the second sectional area such that the second portion constitutes an air passage rate adjustment part.

6. The air ion measuring device according to claim 1, further comprising an air quantity adjustment part disposed in the air passage right ahead of or right behind the location of an air withdrawal fan.

7. The air ion measuring device according to claim 1, wherein the ion detector has a casing made of a resin material, with an outer fitting made of an electrically conductive material fitted outside the casing to form a double-wall structure.

8. The air ion measuring device according to claim 1, further comprising:
    a resin material casing,
    wherein a hollow part is formed in the ion detector between the charge collector electrode and the resin material casing, and between the first and second repelling electrodes and the resin material casing.

9. The air ion measuring device according to claim 1, further comprising an ion detecting circuit including a detecting part disposed in the vicinity of a contact of the charge collector electrode.

10. The air ion measuring device according to claim 1, further comprising a display operable to display positive and negative ion data graphically and as numerical values.

11. The air ion measuring device according to claim 1, further comprising sensors and a time IC, and a display operable to display data such as temperature, relative humidity, date, time and atmospheric air pressure from the sensors and time IC.

12. The air ion measuring device according to claim 1, further comprising a numerical display part operable to display battery usage, detector abnormality, and cautions other than working environments.

* * * * *